(12) United States Patent
Wiser et al.

(10) Patent No.: US 8,827,445 B1
(45) Date of Patent: Sep. 9, 2014

(54) DEVICES AND METHODS FOR A CONTACT LENS WITH AN OUTWARD FACING LIGHT SOURCE

(71) Applicant: Google Inc., Mountain View, CA (US)

(72) Inventors: Robert Francis Wiser, Mountain View, CA (US); Brian Otis, Mountain View, CA (US); Andrew Nelson, Mountain View, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/027,969

(22) Filed: Sep. 16, 2013

Related U.S. Application Data

(63) Continuation of application No. 13/931,394, filed on Jun. 28, 2013.

(51) Int. Cl.
  *G02C 7/04* (2006.01)
  *G02C 11/00* (2006.01)
  *G02F 1/01* (2006.01)

(52) U.S. Cl.
  CPC .............. *G02C 11/10* (2013.01); *G02F 1/0121* (2013.01); *G02C 7/04* (2013.01)
  USPC ...................................... 351/159.02; 351/158

(58) Field of Classification Search
  CPC ......... G02C 11/10; G02C 7/04; G02F 1/0121
  USPC .................. 351/158, 159.01, 159.02, 159.03, 351/159.39
  See application file for complete search history.

(56) References Cited

U.S. PATENT DOCUMENTS

| | | | |
|---|---|---|---|
| 5,297,554 A | 3/1994 | Glynn et al. | |
| 5,682,210 A | 10/1997 | Weinch | |
| 8,096,654 B2 * | 1/2012 | Amirparviz et al. | ....... 351/159.4 |
| 8,446,341 B2 | 5/2013 | Amirparviz et al. | |
| 2009/0189974 A1 | 7/2009 | Deering | |
| 2010/0001926 A1 | 1/2010 | Amirparviz et al. | |
| 2010/0103368 A1 | 4/2010 | Amirparviz et al. | |
| 2012/0199995 A1 | 8/2012 | Pugh et al. | |
| 2012/0245444 A1 | 9/2012 | Otis et al. | |

FOREIGN PATENT DOCUMENTS

| | | |
|---|---|---|
| JP | 8154897 A | 6/1996 |
| WO | 2004015460 A2 | 2/2004 |
| WO | 2011094758 A2 | 8/2011 |

OTHER PUBLICATIONS

Babak A. Parviz, "For Your Eye Only", IEEE Spectrum, Sep. 2009.
Lingley et al., "A single-pixel wireless contact lens display", Journal of Micromechanics and Mocroengineering, 2011.
Mike Flacy, "Researchers Develop LCD Contact Lens that Display Your Text Messages", Digital Trends, Dec. 8, 2012.

* cited by examiner

*Primary Examiner* — Huy K Mai
(74) *Attorney, Agent, or Firm* — McDonnell Boehnen Hulbert & Berghoff LLP

(57) ABSTRACT

A body-mountable device can include a transparent material and a substrate at least partially embedded in the transparent material. The transparent material can have a mounting surface and a surface opposite the mounting surface. A light source can be disposed on the substrate and configured to emit light through the surface opposite the mounting surface. The light source can be controlled by circuitry disposed on the substrate. The circuitry can be configured to receive modulation instructions and modulate the light emitted by the light source based on the modulation instructions.

5 Claims, 11 Drawing Sheets

DEVICES AND METHODS FOR A CONTACT LENS WITH AN OUTWARD FACING LIGHT SOURCE

CROSS REFERENCE TO RELATED APPLICATIONS

The present application is a continuation of U.S. patent application Ser. No. 13/931,394, filed Jun. 28, 2013, which is currently pending. The entire disclosure contents of this application are herewith incorporated by reference into the present application.

BACKGROUND

Unless otherwise indicated herein, the materials described in this section are not prior art to the claims in this application and are not admitted to be prior art by inclusion in this section.

A contact lens device can include a sensor for measuring an analyte, such as glucose, in a tear film. The sensor can be an electrochemical sensor that includes a working electrode and a counter and/or reference electrode. An electrochemical reaction involving the analyte can transfer electrons to or from the working electrode so as to generate a current related to the concentration of the analyte. In some instances, a reagent can be located proximate to the working electrode to facilitate a selective, electrochemical reaction with the analyte.

A contact lens device can also communicate sensor readings to an external reader. For example, the contact lens can include an antenna that is configured to receive radio frequency radiation from the external reader and produce a backscatter signal based on a sensor reading.

SUMMARY

In one example, a body-mountable device is provided that comprises a transparent material having a mounting surface and a surface opposite the mounting surface. The device also comprises a substrate at least partially embedded in the transparent material. The device also comprises a light source disposed on the substrate and at least partially embedded in the transparent material. The light source can be configured to emit light through the surface opposite the mounting surface. The device also comprises circuitry disposed on the substrate. The circuitry can be configured to receive modulation instructions and modulate, based on the modulation instructions, the light emitted by the light source to provide modulated light. The modulated light can be indicative of a human-discernible or machine-readable message from the body-mountable device In another example, a method performed by a body-mountable device is provided. The method comprises receiving modulation instructions in the body-mountable device. The body-mountable device includes a transparent material. The transparent material can have a mounting surface and a surface opposite the mounting surface. The body-mountable device further includes a substrate at least partially embedded in the transparent material. The body-mountable device can also include a light source disposed on the substrate. The method further comprises modulating, based on the modulation instructions, light emitted by the light source to provide modulated light. The method further comprises emitting the modulated light through the surface opposite the mounting surface. The modulated light can be indicative of a human-discernible or machine-readable message from the body-mountable device.

In another example, a method performed by a reader device is provided. The method comprises receiving an incident signal transmitted by a body-mountable device. The body-mountable device includes a transparent material. The transparent material can have a mounting surface and a surface opposite the mounting surface. The body-mountable device further includes a substrate at least partially embedded in the transparent material. The body-mountable device can also include a light source disposed on the substrate. The incident signal comprises light emitted by the light source and transmitted through the surface opposite the mounting surface. The method further comprises determining, based on the incident signal, a message from the body-mountable device.

These as well as other aspects, advantages, and alternatives, will become apparent to those of ordinary skill in the art by reading the following detailed description, with reference where appropriate to the accompanying figures.

DETAILED DESCRIPTION

Figure 1:
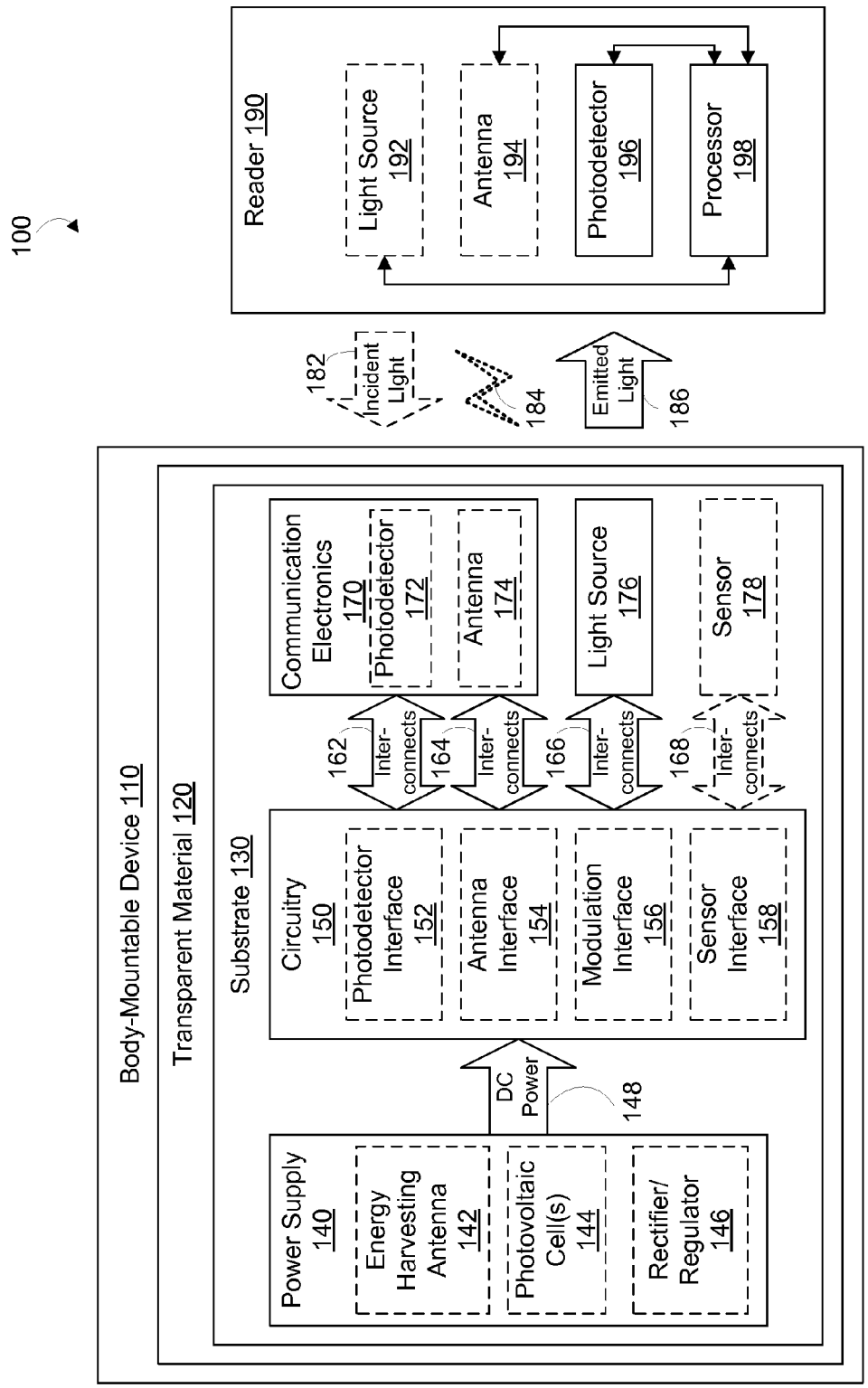
FIG. 1 is a block diagram of an example system 100 that includes a body-mountable device in wireless communication with an external reader.

The following detailed description describes various features and functions of the disclosed systems and methods with reference to the accompanying figures. In the figures, similar symbols identify similar components, unless context dictates otherwise. The illustrative system, device and method embodiments described herein are not meant to be limiting. It may be readily understood by those skilled in the art that certain aspects of the disclosed systems, devices and methods can be arranged and combined in a wide variety of different configurations, all of which are contemplated herein.

An electronic device may be utilized to communicate information to other devices or people. The electronic device could be a body-mountable device. In an example embodiment, the body-mountable device is an eye-mountable device that can be mounted to an eye. In other examples, the body-mountable device could be mounted to a tooth, skin, or other body part. To communicate information, the body-mountable device may include a light source and circuitry to operate the light source. The circuitry and light source may be situated on a substrate embedded in a biocompatible material that includes a mounting surface, which may be used to mount the body-mountable device to an eye or other body part, and a surface opposite the mounting surface. The light source may be configured to emit light through the surface opposite the mounting surface, so that the light is emitted in a direction away from the eye or other body part on which the body-mountable device may be mounted.

The biocompatible material could be a transparent material. For example, the light source may be arranged to emit light through the transparent material so that the light is visible to an external device or to a person viewing the body-mountable device. Alternatively, the biocompatible material could be a non-transparent material or could include a transparent portion and a non-transparent portion. For example, the light source may be arranged so as to emit light through a transparent portion of the biocompatible material.

In some examples, the body-mountable device is an eye-mountable device, and the biocompatible material is a transparent material in the form of a round lens with a concave surface, which can be removably mounted on a corneal surface of an eye, and a convex surface, which faces outward, away from the eye, when the concave surface is mounted on the corneal surface. In this example, the substrate may be embedded near the periphery of the transparent material to avoid interference with incident light received closer to the central region of the eye. In this example, the light source can be arranged on the substrate to face outward, away from the corneal surface, so as to emit light through the convex surface and away from the eye.

In some examples, the light source is entirely embedded within the transparent material. In some examples, the circuitry may be configured to cause the light source to emit modulated light that indicates a message from the body-mountable device. For example, the body-mountable device may include a sensor that can obtain a reading related to an analyte concentration (e.g., a glucose concentration), temperature, or other parameter, and the modulated light may be indicative of the reading obtained by the sensor.

The body-mountable device can be powered via radiated energy harvested at the body-mountable device. Power can be provided by light energizing photovoltaic cells included in the body-mountable device. Additionally or alternatively, power can be provided by radio frequency energy harvested from an antenna included in the body-mountable device. A rectifier and/or regulator can be incorporated in the circuitry to generate a stable DC voltage to power the body-mountable device from the harvested energy. The antenna can be arranged as a loop of conductive material with leads connected to the circuitry. In some embodiments, such a loop antenna can also wirelessly communicate between the body-mountable device and an external reader by modifying the impedance of the loop antenna so as to modify radiation from the antenna.

The light emitted by the light source may be modulated by the circuitry by modifying an aspect of the light. For example, color, brightness, intensity or duration of the light emitted by the light source may be modulated such that the modulated light is indicative of a message. For example, the modulated light may include a series of light pulses that are indicative of a reading of the sensor. In another example, the color of the modulated light may indicate a status of the body-mountable device or a status of components included in the body-mountable device.

Within examples described herein, the body-mountable device may also include a photodetector configured to receive an incident light signal. The received modulation instructions can be based on the incident light signal. For example, the external reader may comprise a computing device. The computing device may emit the incident light signal to request information from the body-mountable device. For example, the incident light signal may indicate that the body-mountable device communicate the reading of the sensor. The body-mountable device may be configured to modulate light emitted by the light source to indicate the reading of the sensor. In some examples, the reader can include a reader photodetector to receive the modulated light and determine a message (e.g., the reading of the sensor) from the body-mountable device.

Some embodiments of the present disclosure therefore provide systems and methods for intermittently communicating information by modulating the light emitted by the light source. Such an intermittent scheme may reduce total power consumption, because the circuitry and the light source are only powered when the communication is necessary.

In some embodiments, the external reader may be configured to provide radio frequency radiation that may be harvested to power the body-mountable device. In some examples, the external reader may be configured to provide light that the photovoltaic cells are configured to harvest power from. Additionally or alternatively, the photovoltaic cells may harvest power from ambient light surrounding the body-mountable device.

FIG. 1 is a block diagram of an example system 100 that includes a body-mountable device 110 in wireless communication with an external reader 190. The exposed regions of the body-mountable device 110 can be made of a transparent material 120 formed to be mounted to a body. In some examples, the transparent material 120 can be contact-mounted to the body. In other examples, the transparent material 120 can be embedded in the body (e.g., surgically embedded, etc.). The transparent material 120 can have a mounting surface and a surface opposite the mounting surface. A substrate 130 is embedded in the transparent material 120 to provide a mounting surface for a power supply 140, circuitry 150, communication electronics 170, and light source 176. In some embodiments, substrate 130 further comprises a sensor 178 also mounted on the substrate 130. The power supply 140 supplies operating voltages to the circuitry 150. The circuitry 150 provides power and controls the communication electronics 170 and light source 176. The light source 176 is operated by circuitry 150 to provide modulated light. The communication electronics 170 are operated by circuitry 150 to communicate information to and/or from the body-mountable device 110. In some embodiments, the antenna 174 is operated by circuitry 150 to communicate the information to and/or from the body-mountable device 110. Additionally or alternatively, the photodetector 172 and the light source 176 can be operated by the circuitry 150 to communicate the information to and/or from the body-mountable device 110. In some embodiments, the sensor 178 receives power and is also operated by circuitry 150 to provide a reading that may be communicated to and/or from the body-mountable device 110.

In some examples where the body-mountable device 110 is an eye-mountable device configured to be contact-mounted to an eye, to facilitate contact-mounting, the transparent material 120 can have a concave surface configured to adhere ("mount") to a moistened corneal surface (e.g., by capillary forces with a tear film coating the corneal surface). Additionally or alternatively, the body-mountable device 110 can be adhered by a vacuum force between the corneal surface and the transparent material 120 due to a concave curvature of the mounting surface of the body-mountable device 110. In this example, while mounted with the concave surface against the eye, the outward-facing surface of the transparent material 120 can have a convex curvature that is formed to not interfere with eye-lid motion while the body-mountable device 110 is mounted to the eye. For example, the transparent material 120 can be a curved polymeric disk shaped similarly to a contact lens.

In some examples, the transparent material 120 can include one or more biocompatible materials. For example, biocompatible materials employed for use in contact lenses or other ophthalmic applications involving direct contact with a body can be used. The transparent material 120 can optionally be formed in part from such biocompatible materials or can include an outer coating with such biocompatible materials. The transparent material 120 can optionally include materials configured to moisturize a surface of the body, such as hydrogels and the like. In some embodiments where the body-mountable device is an eye-mountable device, the transparent material 120 can be shaped to provide a predetermined, vision-correcting optical power, such as can be provided by a contact lens.

The substrate 130 includes one or more surfaces suitable for mounting the power supply 140, circuitry 150, communication electronics 170, and light source 176. In some embodiments, the one or more surfaces are also suitable for mounting sensor 178. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, through hole pads may be patterned and/or drilled on to the substrate 130 to allow connections between components on more than one side of the substrate 130. For example, some components like circuitry 150 and communication electronics 170 may be disposed on one side of the substrate 130 and other components like the light source 176 may be disposed on another side of the substrate 130. In some embodiments, the substrate 130 may be a multilayer substrate (e.g., printed circuit board) that allows connections between components included in the body-mountable device 110 in several layers between multiple sides of the substrate 130. In some embodiments, substantially transparent conductive materials (e.g., indium tin oxide) can be patterned on the substrate 130 to form circuitry 150, electrodes, etc. For example, the antenna 174 can be formed by forming a pattern of gold or another conductive material on the substrate 130 by deposition, photolithography, electroplating, etc. Similarly, interconnects 162, 164, 166 between the circuitry 150 and the photodetector 172, antenna 174, and light source 176, respectively, can be formed by depositing suitable patterns of conductive materials on the substrate 130. In some embodiments, interconnects 168 may be similarly formed to connect circuitry 150 with sensor 178.

A combination of microfabrication techniques including, without limitation, the use of photoresists, masks, deposition techniques, and/or plating techniques can be employed to pattern materials on the substrate 130. In some examples, the substrate 130 can be a rigid material, such as polyethylene terephthalate ("PET") or a flexible material, such as polyimide or organic materials configured to structurally support the circuitry 150 and/or chip-based electronics within the transparent material 120. The body-mountable device 110 can alternatively be arranged with a group of unconnected substrates rather than a single substrate. For example, the circuitry 150 can be mounted to one substrate, while the light source 172 is mounted to another substrate and the two can be electrically connected via interconnects 162.

In some embodiments where the body-mountable device 110 is an eye-mountable device, the substrate 130 (and other components included in the body-mountable device 110) can be positioned away from the center of the body-mountable device 110 and thereby avoid interference with light transmission to the central, light-sensitive region of the eye (e.g., avoid field of view of the eye). For example, where the body-mountable device 110 is shaped as a concave-curved disk, the substrate 130 can be embedded around the periphery (e.g., near the outer circumference) of the disk. In some embodiments, however, the substrate 130 can be positioned in or near the central region of the body-mountable device 110. For example, the body-mountable device 110 can be a tooth-mounted device, and the substrate 130 can be embedded in any location inside the transparent material 120. Additionally or alternatively, the substrate 130 (and other components included in the eye-mountable device 110) can be substantially transparent to incoming visible light to mitigate interference with light transmission to the body. For example, the body-mountable device 110 can be a skin-mounted device, and the substrate 130 can be substantially transparent to allow sunlight to reach the skin.

In some embodiments, the substrate 130 can be shaped as a flattened ring with a radial width dimension sufficient to provide a mounting platform for embedded electronics components. The substrate 130 can have a thickness sufficiently small to allow the substrate 130 to be embedded in the transparent material 120 without influencing a shape of the body-mountable device 110. The substrate 130 can have a thickness sufficiently large to provide structural stability suitable for supporting electronics mounted thereon. For example, substrate 130 can be shaped as a ring with a diameter of about 10 millimeters, a radial width of about 1 millimeter (e.g., an outer radius 1 millimeter larger than an inner radius), and a thickness of about 50 micrometers. However, the diameter, radial width and thickness values are provided for explanatory purposes only. In some embodiments, the dimensions of the substrate 130 can be selected according to the size and/or shape of the body-mountable device 110. The substrate 130 can optionally be aligned with a curvature of a surface of the body-mountable device 110.

The power supply 140 is configured to harvest energy to power the circuitry 150, communication electronics 170, and light source 176. In some embodiments, power supply 140 may also be configured to power sensor 178. For example, a radio-frequency energy-harvesting antenna 142 can capture energy from incident radio radiation. Additionally or alternatively, photovoltaic cell(s) 144 (e.g., solar cells) can capture energy from incoming ultraviolet, infrared, visible, and/or invisible radiation. In some embodiments, the incident radio radiation and/or incoming radiation may be ambient radiation in surroundings of the body-mountable device 110. Additionally or alternatively, the incident radio radiation and/or incoming radiation may be from the external reader 190. Furthermore, an inertial power scavenging system can be included to capture energy from ambient vibrations. The energy harvesting antenna 142 can optionally be a dual-purpose antenna that is also used to communicate information from/to the external reader 190. That is, the functions of the antenna 174 and the energy harvesting antenna 142 can be accomplished with a same physical antenna.

In one example, a rectifier/regulator 146 can be used to condition captured energy to a stable DC supply voltage 148 that is supplied to circuitry 150. For example, the energy harvesting antenna 142 can receive incident radio frequency radiation. Varying electrical signals on the leads of the energy harvesting antenna 142 are output to the rectifier/regulator 146. The rectifier/regulator 146 rectifies the varying electrical signals to a DC voltage and regulates the rectified DC voltage to a level suitable for operating circuitry 150. Additionally or alternatively, output voltage from the photovoltaic cell(s) 144 can be regulated to a level suitable for operating the circuitry 150. The rectifier/regulator 146 can include one or more energy storage devices to mitigate high frequency variations in the energy harvesting antenna 142 and/or photovoltaic cell(s) 144. For example, one or more energy storage devices (e.g., capacitors, inductors, etc.) can be connected with the outputs of the rectifier/regulator 146 to regulate the DC supply voltage 148 and/or configured to function as a low-pass filter.

The circuitry 150 is activated when the DC supply voltage 148 is provided to the circuitry 150, and the logic in the circuitry 150 operates the communication electronics 170 to interact with external reader 190. In some embodiments, the logic in circuitry 150 also operates sensor 178 to obtain a reading of the sensor 178. The circuitry 150 can include logic circuitry configured to receive modulation instructions and control light source 176 to provide modulated emitted light 186 based on the modulation instructions. Additionally or alternatively, the circuitry 150 may be configured to receive the modulation instructions through interaction with the photodetector 172, antenna 174 and/or sensor 178.

In one example, the circuitry 150 includes a photodetector interface 152 that is configured to operate photodetector 172 that may be included in the communication electronics 170. The photodetector 172 can be, for example, an active pixel sensor (APS), charge-coupled device (CCD), cryogenic detector, photodiode, photoresistor, phototransistor, camera, or any other sensor of light configured to provide a signal through interconnects 162 indicative of incident light 182 on the body-mountable device 110. The incident light 182 may be visible light or invisible light (ultraviolet, infrared, etc.). The incident light 182 detected by the photodetector 172 may be indicative of a message or of the modulation instructions for the light source 176 included in the body-mountable device 110. For example, the circuitry 150 may modulate light emitted by light source 176 based on the message. In other examples, the circuitry 150 may control components included in the substrate 130 based on the message.

In some instances, the circuitry 150 may include an antenna interface 154 that is configured to operate antenna 174 included in the communication electronics 170 to send and/or receive information via antenna 174. The antenna interface 154 can optionally include one or more oscillators, mixers, frequency injectors, etc. to modulate and/or demodulate information on a carrier frequency to be transmitted and/or received by the antenna 174. In some examples, the body-mountable device 110 is configured to indicate an output from sensor 178 by modulating an impedance of the antenna 174 in a manner that is perceivable by the external reader 190. For example, the antenna interface 154 can cause variations in the amplitude, phase, and/or frequency of radio frequency radiation (RF radiation) 184 from the antenna 174, and such variations can be detected by the reader 190. RF radiation 184 may also include radiation from the reader 190 to the antenna 174. In some examples, the body-mountable device 110 is configured to receive RF radiation 184 from the reader 190 that is indicative of a message or of the modulation instructions for the light source 176. For example, circuitry 150 may modulate light emitted by light source 176 based on the message. In other examples, the circuitry 150 may control components included in the substrate 130 based on the message. The antenna interface 154 can be connected to antenna 174 via interconnects 164.

The circuitry 150 can also include a modulation interface 156 for modulating light emitted by light source 176. The light emitted by light source 176 could be visible light or invisible light (ultraviolet, infrared, etc.). The circuitry 150 can include logic elements and/or controllers implemented in an integrated circuit to form the modulation interface 156. For example, the modulation interface 156 can modify an aspect of the emitted light 186 by light source 176 like color, brightness, intensity, or duration of the emitted light to provide modulated light. The light source 176 may include one or more light emitting diodes (LED), vertical cavity surface emitting lasers (VCSEL), organic light emitting diodes (OLED), liquid crystal displays (LCD), microelectromechanical systems (MEMS), or any other device configured to selectively transmit, reflect, and/or emit light according to information from the modulation interface 156 via the interconnects 166 to provide the modulated emitted light 186. In some examples, the modulation interface 156 can include one or more data lines providing programming information to separately programmed pixels in the light source 176. In some examples, the light source 176 may also include one or more optical elements to direct the emitted light 186 through the surface opposite the mounting surface of the transparent material 120. In examples where the body-mountable device 110 is an eye-mountable device, the light source 176 disposed on the substrate 130 can be configured to emit light through the convex surface (e.g., surface opposite the mounting surface) of the transparent material 120 and away from a corneal surface of an eye when the concave surface (e.g., the mounting surface) of the transparent material 120 is mounted on the corneal surface of the eye.

The circuitry 150 can optionally include a sensor interface 158 for operating a sensor 178. The sensor 178 can be, for example, a bio-sensor configured to measure an analyte in a tear film. For example, the sensor 178 can be a glucose sensor configured to provide a reading relating to glucose level in the tear film. In some examples, the sensor 178 may measure other biological information like blood pressure, temperature, heart rate or psychological state of the user of the body-mountable device 110. For example, the sensor 178 can be configured to measure a frequency of eye-blinks to determine the psychological state of the user. In another example, the sensor 178 can be configured to measure the concentration of an analyte in saliva (e.g., where the body-mountable device 110 is a tooth-mounted device). In some examples, the sensor 178 may measure aspects of a surrounding environment of the user. For example, the sensor 178 may measure the ambient light intensity or humidity of the surrounding environment. In some examples, the received modulation instructions may be based on the reading of the sensor. For example, the circuitry 150 may be configured to modulate the intensity of the emitted light 186 by the light source 176 according to the intensity of ambient light indicated by the reading of the sensor 178. In other examples, the modulated emitted light 186 may be indicative of the reading of the sensor (e.g., red color may indicate high glucose level, blue color may indicate low glucose level, etc.).

The circuitry 150 is connected to the communication electronics 170 via interconnects 162 and 164. For example, where the circuitry 150 includes logic elements implemented in an integrated circuit to form the photodetector 172 and/or the antenna 174, a patterned conductive material (e.g., gold, platinum, palladium, titanium, copper, aluminum, silver, metals, combinations of these, etc.) can connect a terminal on the chip to communication electronics 170. Similarly, the circuitry 150 can be connected to the light source 176 via interconnects 166. In some embodiments, the circuitry 150 can be similarly connected to the sensor 178 via interconnects 168.

It is noted that the block diagram shown in FIG. 1 is described in connection with functional modules for convenience in description. However, embodiments of the body-mountable device 110 can be arranged with one or more of the functional modules ("subsystems") implemented in a single chip, integrated circuit, and/or physical component. For example, while the rectifier/regulator 146 is illustrated in the power supply block 140, the rectifier/regulator 146 can be implemented in a chip that also includes the logic elements of circuitry 150 and/or other features of the embedded electronics in the body-mountable device 110. Thus, the DC supply voltage 148 that is provided to the circuitry 150 from the power supply 140 can be a supply voltage that is provided to components on a chip by rectifier and/or regulator 146 components located on a same chip. That is, the functional blocks in FIG. 1 shown as the power supply block 140 and circuitry block 150 need not be implemented as physically separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same physical antenna. For example, a loop antenna can both harvest incident radiation for power generation and communicate information via backscatter radiation.

The external reader 190 can be a smart phone, digital assistant, head-mounted computing device (e.g., eye glasses with computing capability), or other computing device with wireless connectivity sufficient to provide the RF radiation 184 and/or the incident light 182. The external reader 190 can also be implemented as an antenna module and/or light source module that can be plugged in to a computing device, such as in an example where the RF radiation 184 operates at carrier frequencies not commonly employed in computing devices, or in an example where the computing device does not include a light source. The external reader 190 can also be configured to receive the emitted light 186 from the body-mountable device 110 via a reader photodetector 196. In some instances, the external reader 190 is a special-purpose device configured to be worn relatively near a wearer's body to allow communication via the RF radiation 184 and/or the incident light 182 to operate with a low power budget. For example, the external reader 190 can be integrated in a piece of jewelry such as a necklace, earing, etc. or integrated in an article of clothing worn near the head, such as a hat, headband, eyeglasses, etc.

In an example where the body-mountable device 110 includes the photodetector 172, the external reader 190 may include a reader light source 192 configured to provide modulated incident light 182 to the eye-mountable device 110. For example, the modulated incident light 182 may indicate the received modulation instructions to the circuitry 150 such that the circuitry 150 modulates the emitted light 186 based on the received modulation instructions. In another example, the modulated incident light 182 may include instructions to the body-mountable device 110 to obtain a reading of the sensor 178. Thus, in this example, the circuitry 150 may be configured to modulate the emitted light 186 to provide modulated light indicative of the reading of the sensor. In some examples, the reader 190 can include the reader photodetector 196 to receive the modulated emitted light 186 and determine the reading of the sensor based on the modulated emitted light 186. In some examples, the modulated incident light 182 may be indicative of a status of the reader 190 or components included in the reader 190. In other examples, the modulated emitted light 186 may be indicative of a status of the body-mountable device 110 or a status of components included in the body-mountable device 110. For example, the status of photovoltaic cell(s) 144 may be indicated by the modulated emitted light 186. In some examples, the external reader 190 can provide light to the photovoltaic cell(s) 144 included in the body-mountable device 110 that are configured to harvest the light to provide power to the body-mountable device 110.

In an example where the body-mountable device 110 includes an antenna 174, the external reader 190 may include a reader antenna 194 configured to send and/or receive information from the body-mountable device 110 via the RF radiation 184. For example, the antenna 174 may be configured to send information pertaining to the reading of the sensor 178 through RF radiation 184. Thus, the RF radiation 184 may be received by the reader antenna 194 and the reading of the sensor 178 may be determined by the reader 190 based on the RF radiation 184. In some examples, the reader antenna 194 may transmit information to the body-mountable device 110 via the RF radiation 184. In some examples, the external reader 190 may provide the RF radiation 184 to the energy harvesting antenna 142 included in the body-mountable device 110 that is configured to harvest the RF radiation 184 to provide power to the body-mountable device 110.

The external reader 190 can include a processor 198 configured to control reader light source 192, reader antenna 194, and reader photodetector 196 to perform the functions described in the examples included in the present disclosure. For example, the processor 198 may be configured to modulate light from the reader light source 192 to provide the modulated incident light 182.

In some embodiments, the system 100 can operate to non-continuously ("intermittently") supply energy to the body-mountable device 110 to operate the power supply 140. For example, incident light 182 and/or RF radiation 184 can be supplied to power the eye-mountable device 110 long enough to obtain a reading by the sensor 178 and wirelessly communicate the reading via emitted light 186 and/or RF radiation 184 to the external reader 190. In such an example, the incident light 182 and/or the RF radiation 184 can be considered an interrogation signal from the external reader 190 to the body-mountable device 110 to request a reading. By periodically interrogating the body-mountable device 110 (e.g., by supplying the incident light 182 and/or RF radiation 184 to temporarily turn the device on), the external reader 190 can accumulate a series of readings without continuously powering the body-mountable device 110.

Figure 2A:
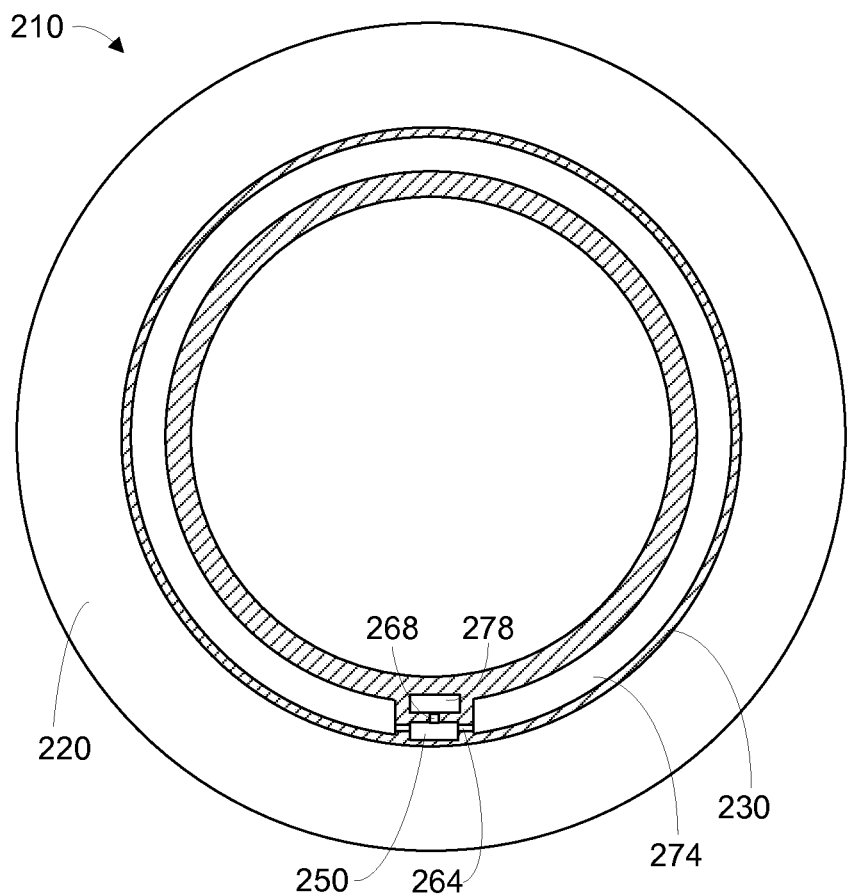
FIG. 2A is a bottom view of an example eye-mountable device 210.
Figure 2B:
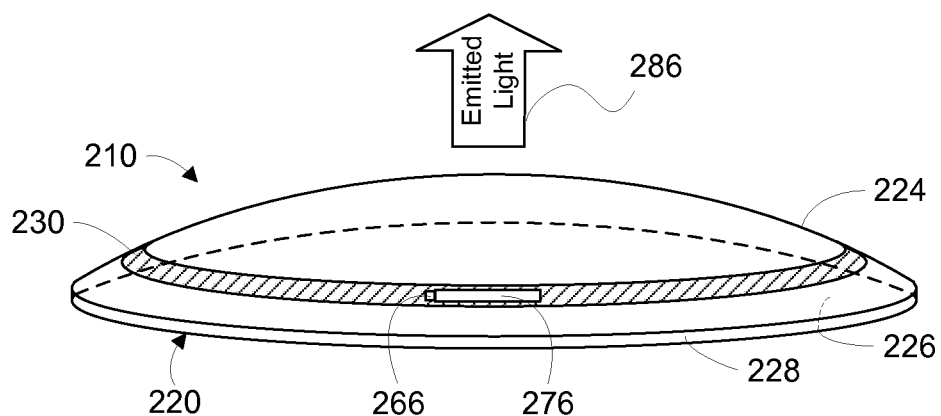
FIG. 2B is a side view of the example eye-mountable device shown in FIG. 2A.

FIG. 2A is a bottom view of an example eye-mountable device 210 ("body-mountable device"). FIG. 2B is a side view of the example eye-mountable device 210 shown in FIG. 2A. It is noted that the relative dimensions in FIGS. 2A and 2B are not necessarily to scale, but have been rendered for purposes of explanation only in describing the arrangement of the example eye-mountable device 210. The eye-mountable device 210 can be formed of a transparent material 220 shaped as a curved disk. The transparent material 220 can allow incident light (e.g., field of view of the eye) to be transmitted to the eye while the eye-mountable device 210 is mounted to the eye. In some examples, the transparent material 220 can be a biocompatible polymeric material similar to those employed to form vision correction and/or cosmetic contact lenses in optometry, such as polyethylene terephthalate (PET), polymethyl methacrylate (PMMA), polyhydroxyethylmethacrylate (polyHEMA), silicone hydrogels, combinations of these, etc. The transparent material 220 can be formed with one side having a concave surface 226 (e.g., "mounting surface", bottom-view surface shown in FIG. 2A, etc.) suitable to fit over a corneal surface of the eye. The opposite side of the disk can have a convex surface 224 ("surface opposite the mounting surface") that does not interfere with eyelid motion while the eye-mountable device 210 is mounted to the eye. A circular outer side edge 228 can connect the concave surface 224 and the convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The transparent material 220 can be formed with a curved shape in a variety of ways. For example, techniques similar to those employed to form vision-correction contact lenses, such as heat molding, injection molding, spin casting, etc. can be employed to form the transparent material 220. When the eye-mountable device 210 is mounted to an eye, the convex surface 224 faces outward to an ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226.

A substrate 230 is embedded in the transparent material 220. In some examples, the substrate 230 can be embedded to be along an outer periphery of the transparent material 220, away from a central region of the eye-mountable device 210. Thus, in this example, the substrate 230 does not interfere with vision because it is too close to the eye to be in focus and is positioned away from the central region where ambient light is transmitted to eye-sensing portions of the eye. In some examples, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections.

In some examples, the substrate 230 and the transparent material 220 can be substantially cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometer. However, these dimensions are provided for example purposes only, and in no way limit the present disclosure. The substrate 230 can be implemented in a variety of different form factors, similar to the discussion of the substrate 130 in connection with FIG. 1 above.

Circuitry 250, a loop antenna 274 and a sensor 278 are disposed on a side of the substrate 230 that is facing the concave surface 226 ("bottom side") of the transparent material 220 as shown in FIG. 2A. A light source 276 is disposed on an opposite side of the substrate 230 that is facing the convex surface 224 of the transparent material 220 ("top side") as shown in FIG. 2B. However, in some embodiments, circuitry 250, the loop antenna 274, the light source 276 and/or the sensor 278 may be disposed on any side of the substrate 230. For example, in some embodiments, the circuitry 250 may be disposed in the opposite side ("top side") of the substrate 230 that is facing the convex surface 224 of the transparent material 220. In one example, the light source 276 may be disposed in the side of the substrate 230 that is facing the concave surface 226 ("bottom side"). In that case, the substrate 230 may include a hole through which light emitted by the light source 276 can reach the convex surface 224 and propagate away from the corneal surface. In some examples, one or more components disposed on the substrate 230 may be disposed on a side of the substrate 230 that is facing the circular outer side edge 228 of the transparent material 220.

In some embodiments not illustrated in FIGS. 2A-2B, the substrate 230 may include multiple layers for interconnects and other conductive material connected to components disposed on the substrate 230. Other configurations of the substrate 230 are contemplated herein and may be obvious to those of ordinary skill in the art. For example, one of the multiple layers may be utilized as "a ground plane" for the components to connect to a ground voltage.

The circuitry 250 may comprise a chip including logic elements configured to operate the loop antenna 274, the light source 276 and the sensor 278. The circuitry 250 is electrically coupled to the loop antenna 274 and the sensor 278, respectively, by interconnects 264 and 268. Interconnects 266 electrically connect the circuitry 250 with the light source 276 through the substrate 230. For example, interconnects 266 may be arranged in a through hole connecting the side of the substrate 230 that is facing the concave surface 226 ("bottom side") of the transparent material 220 to the opposite side of the substrate 230 that is facing the convex surface 224 ("top side") of the transparent material 220. The interconnects 264, 266, 268, and the loop antenna 274 can be formed from conductive materials patterned on the substrate 230 by a process for patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc. The circuitry 250 can be configured to receive modulation instructions and configured to modulate emitted light 286 from the light source 276 based on the received modulation instructions.

The loop antenna 274 can be a layer of conductive material patterned along a flat surface of the substrate to form a flat conductive ring. In some instances, the loop antenna 274 can be formed without making a complete loop. For instance, the loop antenna 274 can have a cutout to allow room for the circuitry 250 and the sensor 278, as illustrated in FIG. 2A. However, the loop antenna 274 can also be arranged as a continuous strip of conductive material that wraps entirely around the flat surface of the substrate 230 one or more times. For example, a strip of conductive material with multiple windings can be patterned on a side of the substrate 230 opposite the circuitry 250 and sensor 278. Thus, in this example, interconnects 264 between the ends of such a wound antenna (e.g., antenna leads) can then be passed through the substrate 230 to the circuitry 250 similarly to interconnects 266 in FIG. 2B.

The light source 276 may include one or more light emitting diodes (LED), vertical cavity surface emitting lasers (VCSEL), organic light emitting diodes (OLED), liquid crystal display (LCD), microelectromechanical system (MEMS), or any other device configured to selectively transmit, reflect, and/or emit light according to received modulation instructions by the circuitry 250 via the interconnects 266 to provide the modulated emitted light 286. Operation of the light source 276 is similar to light source 176 discussed in FIG. 1. The light source 276 is configured to provide the emitted light 286 through the convex surface 224 and away from the corneal surface.

Although illustrated in FIG. 2B that interconnects 266 are connected to one end of the light source 276, some embodiments may include the interconnects 266 connected to any other part of the light source 276. For example, the interconnects 266 may be arranged underneath the light source 276 so that they are not viewable from the "top" side of the eye-mountable device 210 (the side facing the convex surface 224).

The light source 276 may be configured in a rectangular, triangular, circular and/or any shape that is compatible with the flat surface of the substrate 230. For example, the light source 276 may have a loop shape similar to the loop antenna 274. The light source 276 may be configured to provide the emitted light 286 based on the received modulation instructions by the circuitry 250. For example, the emitted light 286 may be indicative of a status of the eye-mountable device 210 or a status of components included in the eye-mountable device 210. For example, the emitted light 286 may be a blinking light that indicates insufficient power being provided to the eye-mountable device 210.

The sensor 278 can be disposed on the substrate 230 and configured to provide a reading to circuitry 250 via interconnects 268. For example, the received modulation instructions may be indicative of the reading of the sensor 278. In some examples, the received modulation instructions may be a response to radio frequency radiation received by the loop antenna 274 indicative of obtaining the reading from the sensor 278.

Figure 2D:
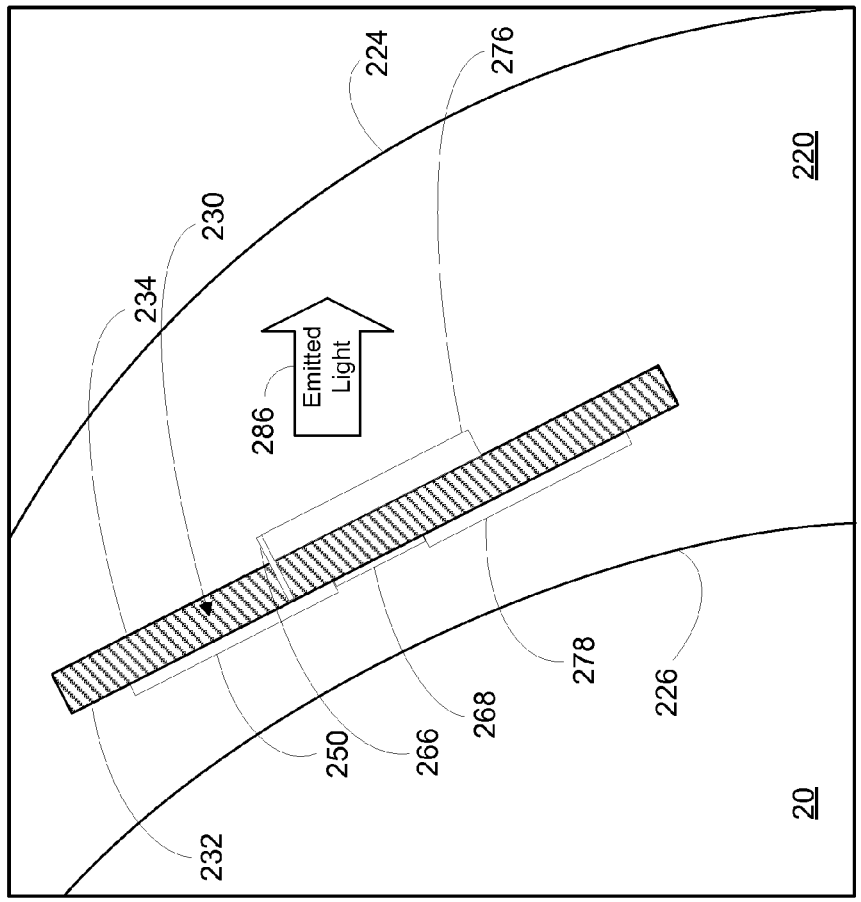
FIG. 2D is a close-in side cross-section view enhanced to show the substrate embedded in the transparent material, the light source, and the emitted light in the example eye-mountable device when mounted as shown in FIG. 2C.
Figure 2C:
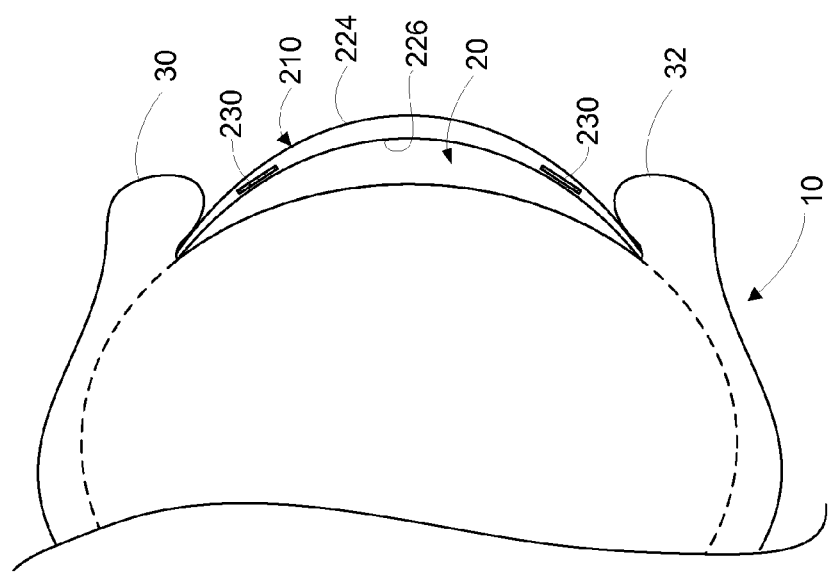
FIG. 2C is a side cross-section view of the example eye-mountable device shown in FIGS. 2A and 2B while mounted to a corneal surface of an eye.

FIG. 2C is a side cross-section view of the example eye-mountable device shown in FIGS. 2A and 2B while mounted to a corneal surface 20 of an eye 10. FIG. 2D is a close-in side cross-section view enhanced to show the substrate 230 embedded in the transparent material 220, the light source 276, and the emitted light 286 in the example eye-mountable device 210 when mounted as shown in FIG. 2C. It is noted that relative dimensions in FIGS. 2C and 2D are not necessarily to scale, but have been rendered for purposes of explanation only in describing the arrangement of the example eye-mountable device 210. Some aspects are exaggerated to allow for illustration and facilitate explanation. It is further noted that the orientation of the substrate 230 embedded in the transparent material 220 is not necessarily as shown in FIG. 2D. In some embodiments, the substrate 230 may be oriented at any angle such that an outward-facing flat mounting surface 234 of the substrate 230 is facing the convex surface 224 of the transparent material 220 and an inward-facing flat mounting surface 232 of the substrate 230 is facing the concave surface 226 of the transparent material 220.

The eye 10 includes a corneal surface 20 that is covered by bringing an upper eyelid 30 and a lower eyelid 32 together over eye 10. Ambient light is received by the eye 10 through the corneal surface 20, where the ambient light is optically directed to light sensing elements of the eye 10 (e.g., rods and cones, etc.) to stimulate visual perception. As illustrated in FIG. 2C, the concave surface 226 is configured to be removably mounted to the corneal surface 20. Additionally, the convex surface 224 is compatible with motion of the eyelids 30 and 32.

As illustrated in FIG. 2D, the emitted light 286 from the light source 276 is directed away from the corneal surface 20 and through the convex surface 224 when the concave surface 226 is mounted on the corneal surface 20. For example, the light source 276 can be disposed on the outward-facing flat mounting surface 234 of the substrate 230 to allow the emitted light 286 to travel through the convex surface 224. In the example, interconnects 266 connect the circuitry 250, disposed on the inward-facing flat mounting surface 232 of the substrate 230, to the light source 276 through the substrate 230.

As shown in the cross-sectional views in FIGS. 2C and 2D, the substrate 230 can be inclined such that the flat mounting surfaces 232 and 234 are approximately parallel to an adjacent portion of the concave surface 226. However, in some embodiments, the substrate 230 can be oriented at any angle such that the outward-facing mounting surface 234 is facing the convex surface 224. As described above, the substrate 230 can be a flattened ring with the inward-facing surface 232 (closer to the concave surface 226 of the transparent material 220) and the outward-facing surface 234 (closer to the convex surface 224). The substrate 230 can have electronic components and/or patterned conductive materials mounted to either or both mounting surfaces 232, 234 or through the substrate 230 to connect components from one surface to another.

Figure 3:
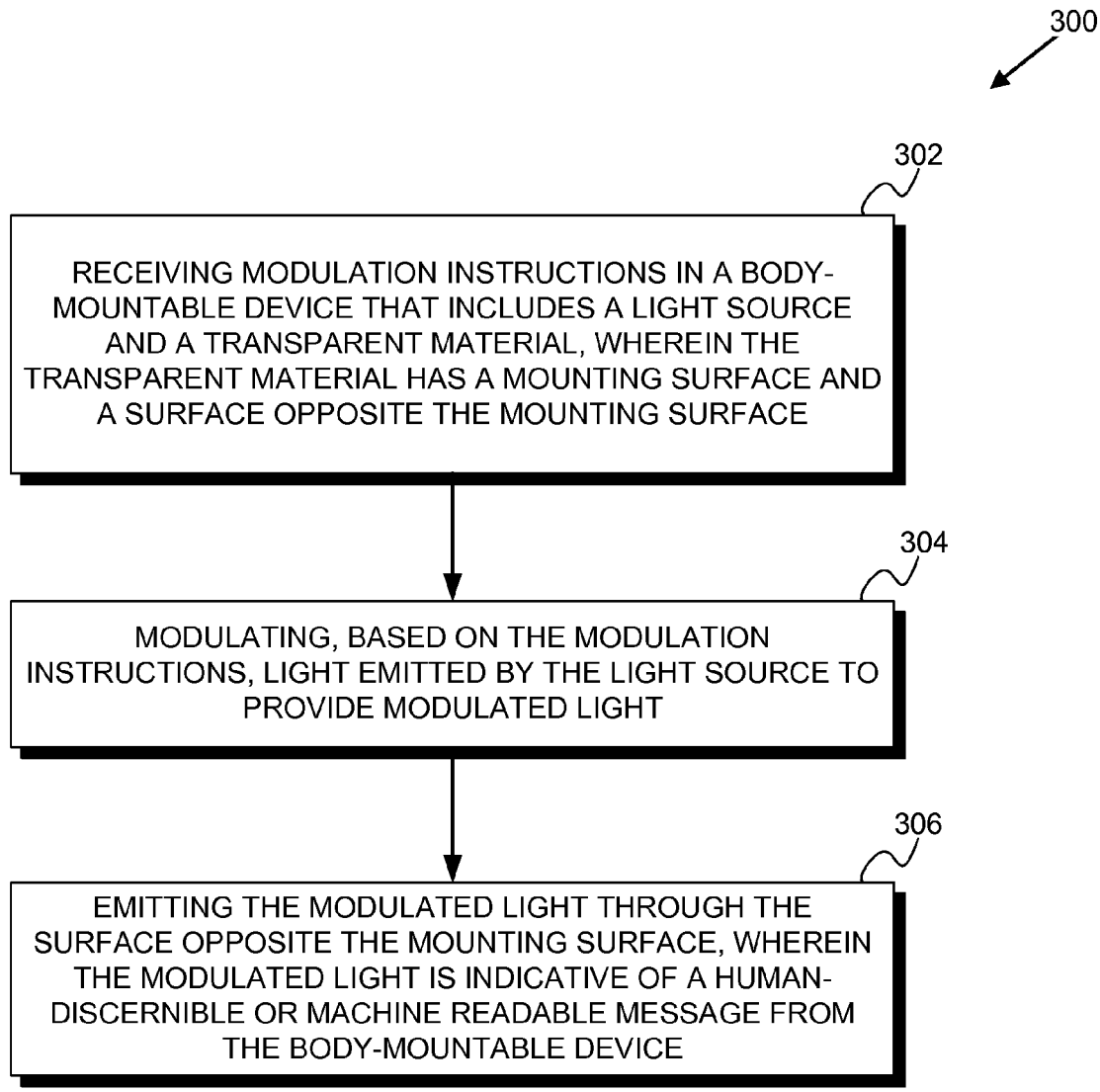
FIG. 3 is a block diagram of an example method 300 for operating a body-mountable device, in accordance with at least some embodiments described herein.

FIG. 3 is a block diagram of an example method for operating a body-mountable device, in accordance with at least some embodiments described herein. Method 300 shown in FIG. 3 presents an embodiment of a method that could be used with the devices 110, and 210, for example. Method 300 may include one or more operations, functions, or actions as illustrated by one or more of blocks 302-306. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 300 and other processes and methods disclosed herein, the flowchart shows functionality and operation of one possible implementation of present embodiments. In this regard, each block may represent a module, a segment, or a portion of a manufacturing or operation process.

At block 302, the method 300 includes receiving modulation instructions in a body-mountable device that includes a light source and a transparent material, wherein the transparent material has a mounting surface and a surface opposite the mounting surface.

In some examples, the received modulation instructions can be generated by circuitry included in the body-mountable device. In one example, the circuitry can generate the modulation instructions based on a status of the body-mountable device (e.g., low power available, malfunctioning component, etc.). In another example, the circuitry can generate the modulation instructions based on a reading of a sensor included in the body-mountable device (e.g., a high glucose reading of a glucose sensor). In another example, the circuitry can generate the modulation instructions based on data and/or instructions received from an external device (e.g., a reader, a computing device, etc.). For example, the data can indicate a time of day, and the circuitry can generate the modulation instructions to modulate the light to a color suitable for the time of day (e.g., green at morning, blue at midday, red at night, etc.).

Additionally or alternatively, in some examples, the body-mountable device can receive the modulation instructions from an external device (e.g., head-mounted device, mobile phone, computing device, etc.). For example, the external device can send the modulation instructions indicative of modulating the light to a certain color or brightness (e.g., for aesthetic purposes). In some examples, the external device can send the modulation instructions via radio frequency radiation (RF radiation), and the body-mountable device can include an antenna configured to receive the RF radiation. In some examples, the external device can send the modulation instructions via an incident light signal from a light source included in the external device, and the body-mountable device can include a photodetector configured to receive the incident light signal.

At block 304, the method 300 includes modulating, based on the modulation instructions, light emitted by the light source to provide modulated light.

At block 306, the method 300 includes emitting the modulated light through the surface opposite the mounting surface, wherein the modulated light is indicative of a human-discernible or machine readable message from the body-mountable device.

For example, the body-mountable device may include a sensor configured to provide a measurement of an analyte in a tear film of an eye (e.g., glucose) when the body-mountable device is mounted on the eye. Thus, the method 300 could include generating and/or receiving the modulation instructions based on the reading of the sensor (step 302), modulating the light emitted (step 304) by the light source (e.g., red color for high reading, green color for normal reading, blue color for low reading), and emitting the modulated light (step 306) through the convex surface (e.g., surface opposite the mounting surface) and away from the eye (similarly to the emitted light 286 in the embodiment illustrated in FIG. 2D). In some examples, the modulated light can be indicative of a message from the body-mountable device. In some examples, the message may relate to a status of the body-mountable device (e.g., low power remaining).

Although not illustrated in FIG. 3, in some examples, the body-mountable device may include a photodetector. The method 300 may receive the modulation instructions based on incident light on the photodetector. For example, a hand-held mobile device may emit infrared light towards the body-mountable device that corresponds to the modulation instructions. In such an example, the infrared light may relate to changing the color of the light emitted by the body-mountable device (e.g., for aesthetic purposes). The body-mountable device may then modify the color of the emitted light based on the received modulation instructions.

Figure 4:
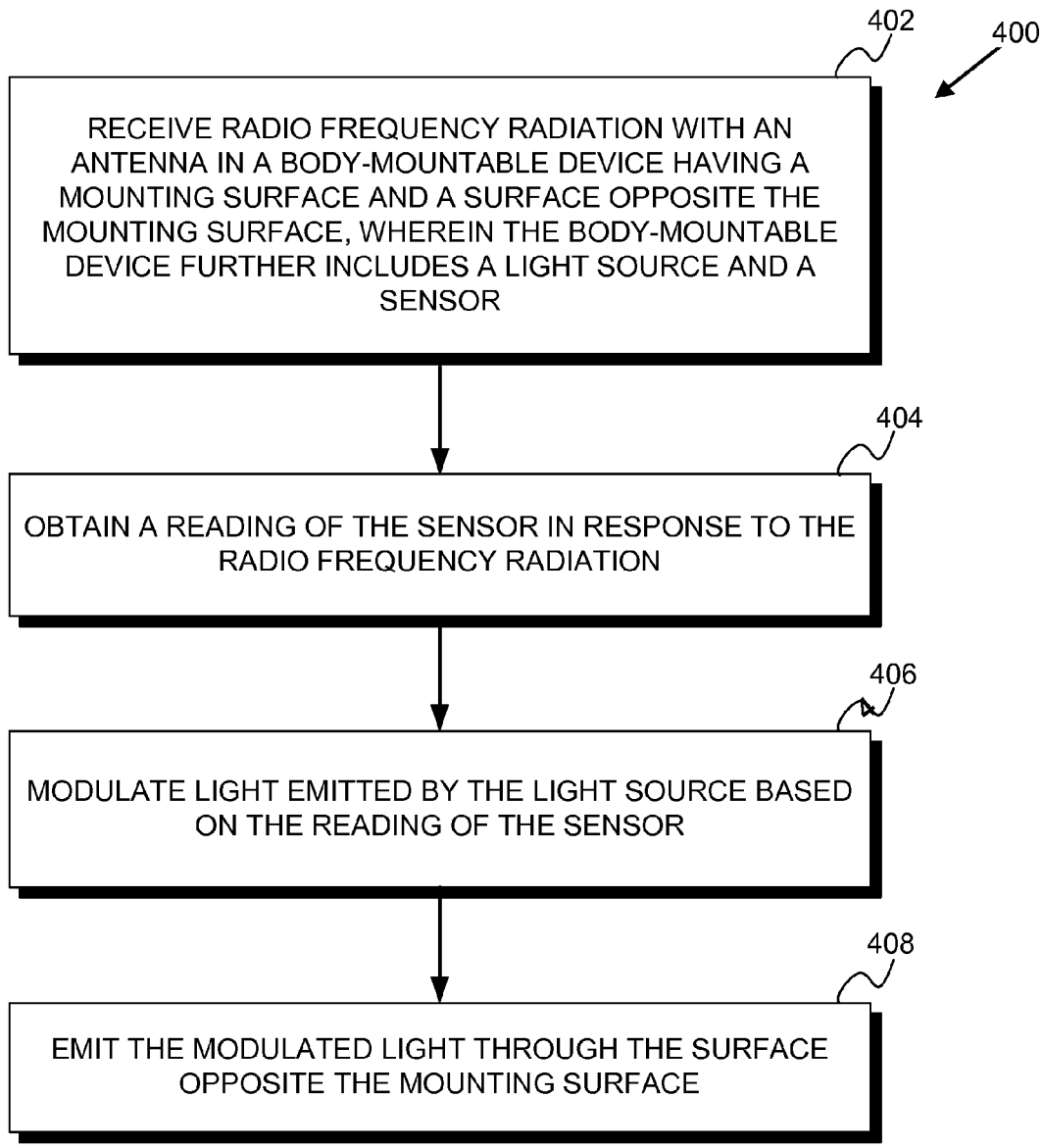
FIG. 4 is a block diagram of an example method 400 for operating a body-mountable device via an antenna, in accordance with at least some embodiments described herein.

FIG. 4 is a block diagram of an example method for operating a body-mountable device via an antenna, in accordance with at least some embodiments described herein. Method 400 shown in FIG. 4 presents an embodiment of a method that could be used with the devices 110, and 210, for example. Method 400 may include one or more operations, functions, or actions as illustrated by one or more of blocks 402-408. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 400 and other processes and methods disclosed herein, the flowchart shows functionality and operation of one possible implementation of present embodiments. In this regard, each block may represent a module, a segment, or a portion of a manufacturing or operation process.

At block 402, radio frequency radiation is received at an antenna in a body-mountable-device including an embedded outward-facing light source. The body-mountable device has a mounting surface and a surface opposite the mounting surface. The eye-mountable device further comprises a sensor.

At block 404, the body-mountable device obtains a reading of the sensor in response to the radio frequency radiation (e.g., the radio frequency radiation may provide power to the body-mountable device or a request to obtain the reading).

At block 406, the body-mountable device modulates light emitted by the light source based on the reading of the sensor (e.g., modify color of light according to the reading).

At block 408, the body-mountable device emits the modulated light through the surface opposite the mounting surface.

In one example, the radio frequency radiation may pertain to modulation instructions ("message") for the body-mountable device (step 402). For example, the radio frequency radiation may define the modulation of light according to each sensor reading (e.g., define color for low reading, define color for high reading, etc.). Thus, in this example, the body-mountable device may then modulate the light emitted by the light source based on the reading of the sensor and according to the modulation instructions (step 406). The light source may then emit the modulated light through the surface opposite the mounting surface so that people around a user of the body-mountable device may be alerted by the sensor measurement about the user of the body-mountable device.

Figure 5A:
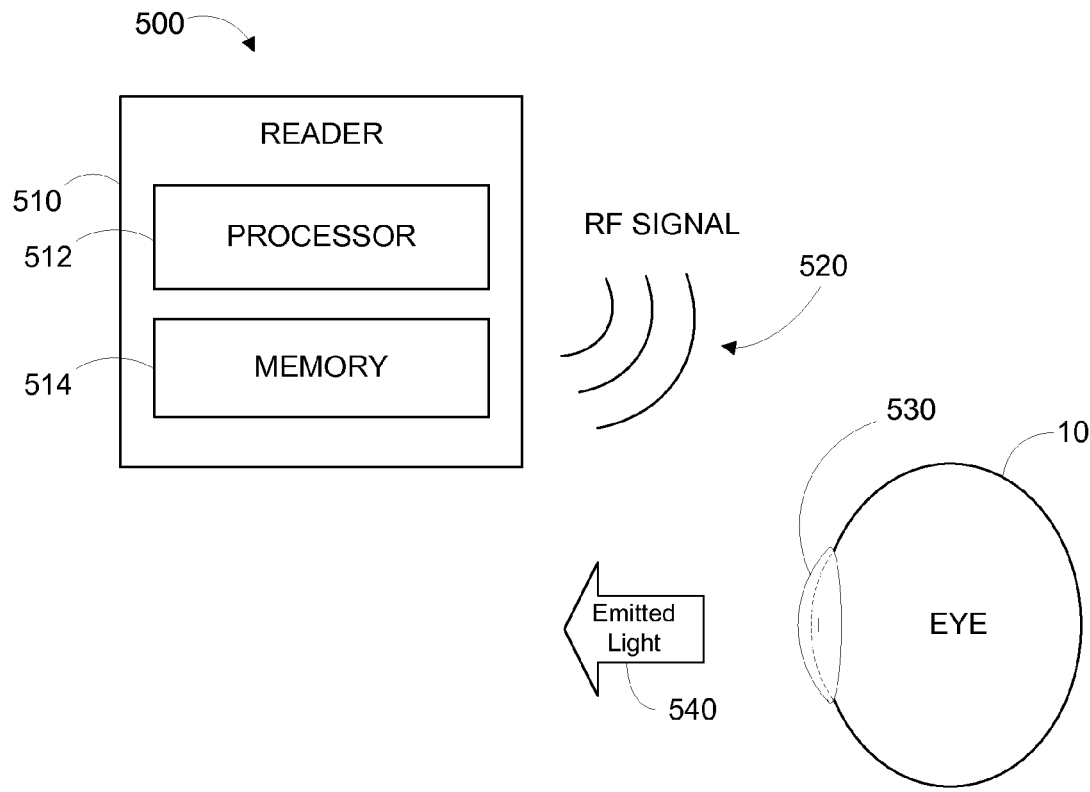
FIG. 5A is a block diagram of an example system 500 with an eye-mountable device that includes an outward facing light source and is operated by an external reader.

FIG. 5A is a block diagram of an example system 500 with an eye-mountable device 530 ("body-mountable device") that includes an outward facing light source and is operated by an external reader 510. The eye-mountable device 530 can be configured to be contact-mounted over a corneal surface of an eye 10. The eye-mountable device 530 can be configured to receive modulation instructions from the external reader 510, and modulate emitted light 540.

The external reader 510 includes a processor 512 and a memory 514. The processor 512 can be a computing system that executes software stored in the memory 514 to cause system 500 to operate, as described herein, the eye-mountable device 530. The external reader 510 can also include an antenna (not shown) for transmitting radio frequency radiation 520 (RF radiation) that is received by the eye-mountable device 530. For example, the RF radiation 520 may correspond to the received modulation instructions. The external reader 510 can be configured to provide the modulation instructions to modify an aspect of the emitted light 540 (e.g., color, brightness, intensity, duration, etc.).

For instance, the external reader 510 may be a hand-held computing device (e.g. mobile phone, personal digital assistant, etc.). In such an example, a user of system 500 may select the appearance (color, intensity, frequency, etc.) of the emitted light 540 as the user wishes. For example, the user may want to change the aesthetic appearance of the eye-mountable device 530 by selecting brighter light, different color, etc. Thus, the external reader 510 can send modulation instructions to the eye-mountable device 530 pertaining to the selected modulation by the user. As a result, the eye-mountable device 530 can modulate the emitted light 540 to reflect the user's selections. In other examples, the modulation instructions may be determined based on instructions in the memory 514. For example, the modulation instructions may be indicative of an appointment in a calendar of the user determined by the external reader 510. For example, the eye-mountable device 530 may modulate the emitted light 540 (e.g. flashing red light) to indicate to people around the user that the user has an upcoming appointment.

Figure 5B:
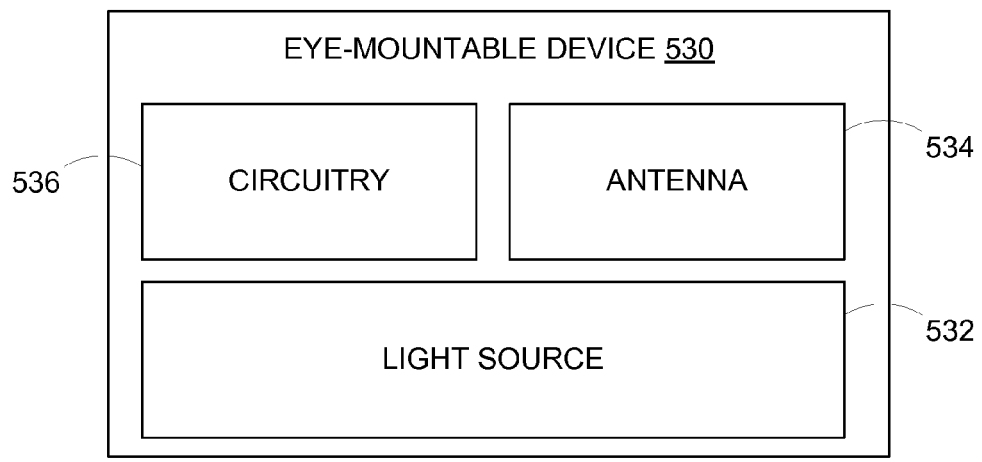
FIG. 5B is a block diagram of the eye-mountable device 530 described in connection with FIG. 5A.

FIG. 5B is a block diagram of the eye-mountable device 530 described in connection with FIG. 5A. The eye-mountable device 530 includes the outward facing light source 532, an antenna 534, and circuitry 536. The outward-facing light source 532 provides the emitted light 540 as described in FIG. 5A. The antenna 534 can be configured to receive the RF signal 520 (shown in FIG. 5A) that pertains to the modulation instructions. Circuitry 536 can be configured to determine the modulation instructions based on the received RF signal 520. Circuitry 536 can also be configured to modulate the emitted light 540 by controlling the light source 532.

Figure 6A:
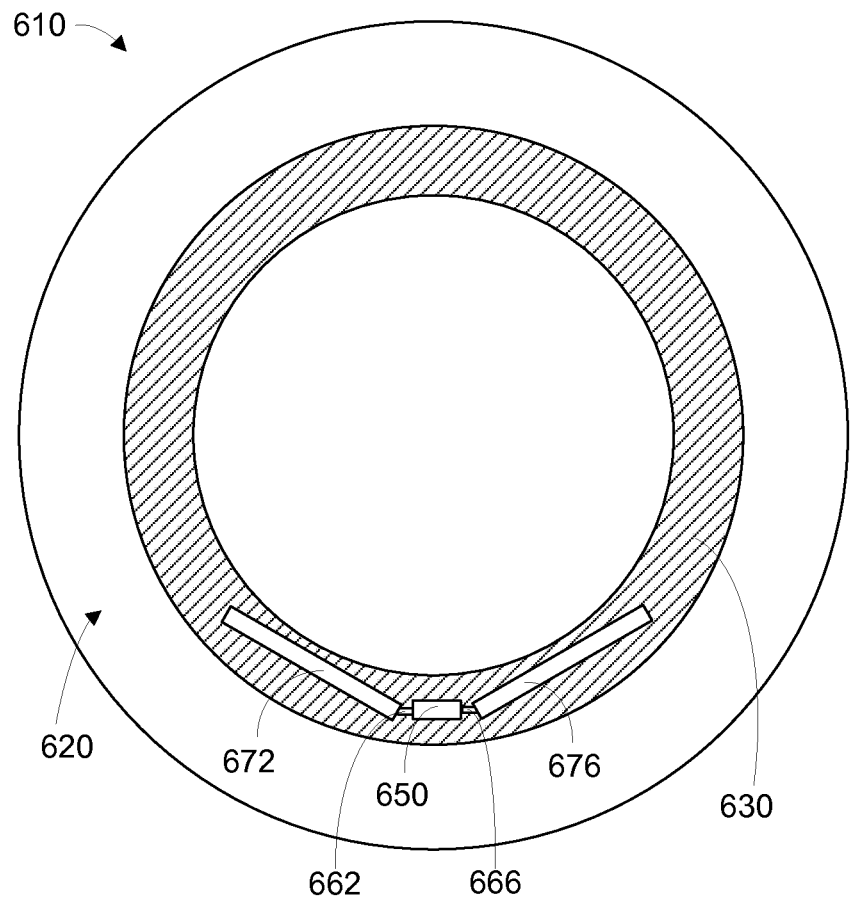
FIG. 6A is a top view of an example eye-mountable device 610.
Figure 6B:
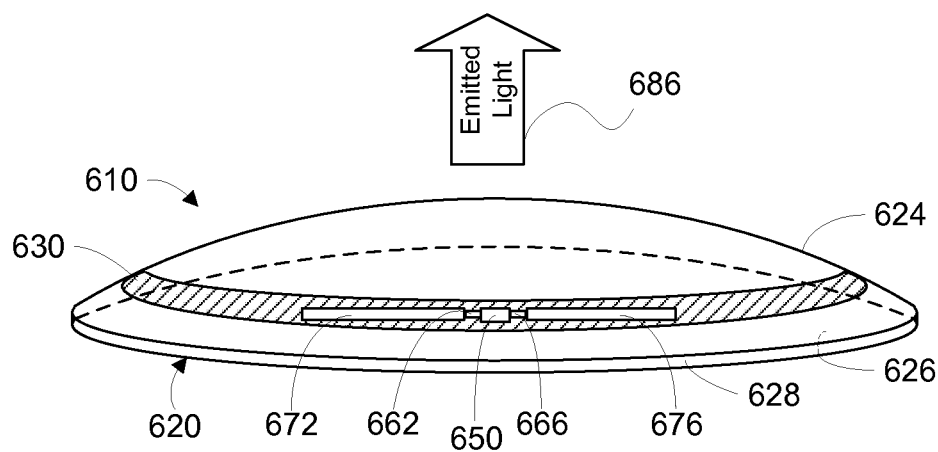
FIG. 6B is a side view of the example eye-mountable device shown in FIG. 6A.

FIG. 6A is a top view of an example eye-mountable device 610 ("body-mountable device"). FIG. 6B is a side view of the example eye-mountable device 610 shown in FIG. 6A. It is noted that the relative dimensions in FIGS. 6A and 6B are not necessarily to scale, but have been rendered for purposes of explanation only in describing the arrangement of the example eye-mountable device 610.

The composition, arrangement, and shape of a transparent material 620, substrate 630, and interconnects 662, 666 included in the eye-mountable device 610 is similar to the transparent material 220, substrate 230, and interconnects 264, 266, 268 discussed in device 210. Similarly, the transparent material 620 can be formed with one side having a concave surface 626 ("mounting surface") suitable to fit over a corneal surface of an eye. The opposite side of the disk (top-view surface shown in FIG. 6A) can have a convex surface 624 ("surface opposite the mounting surface") that does not interfere with eyelid motion while the eye-mountable device 210 is mounted to the eye. A circular outer side edge 628 connects the concave surface 624 and the convex surface 626. The eye-mountable device 610 can have dimensions similar to the eye-mountable device 210 discussed in the description of FIGS. 2A-2D. When the eye-mountable device 610 is mounted to the eye, the convex surface 624 faces outward to a surrounding environment while the concave surface 626 faces inward, toward the corneal surface. The convex surface 624 can therefore be considered an outer, top surface of the eye-mountable device 610 whereas the concave surface 626 can be considered an inner, bottom surface. The "top" view shown in FIG. 6A is facing the convex surface 624.

Circuitry 650, light source 676, and photodetector 672 are disposed on the top surface of the substrate 630 (surface that is closer to the convex surface 624). Interconnects 662 and 666 connect circuitry 650, respectively, with the photodetector 672 and the light source 676.

The photodetector 672 is similar to the photodetector 172 discussed in system 100. The photodetector 672 may be configured to receive incident light that pertains to modulation instructions for the eye-mountable device 610. The incident light may be invisible light (infrared, ultraviolet, etc.) or visible light. The photodetector 672 can transmit an electrical signal indicative of the incident light through interconnects 662 to the circuitry 650.

Circuitry 650 can be configured to receive the electrical signal from the photodetector 672 and determine, based on the electrical signal, modulation instructions for emitted light 686. The circuitry may then modulate the emitted light 686 by controlling the light source 676 via interconnects 666. Additionally or alternatively, the circuitry 650 may control one or more components included in the eye-mountable device 610 based on the electrical signal.

The light source 676 is similar to the light source 276 discussed in the eye-mountable device 210 of FIGS. 2A-2D. The light source 676 can provide the emitted light 686, based on the modulation instructions received from the circuitry.

In some examples, the example eye-mountable device 610 may receive incident light from an external computing device not shown in FIGS. 6A-6B. For example, the external computing device may interrogate the eye-mountable device 610 on a status of the eye-mountable device 610 by conveying a message through the incident light that is received by the photodetector 672. In one example, the circuitry 650 may determine that the eye-mountable device is low on power based on a measurement of the current going through one or more component. Thus, the circuitry 650 can modulate the emitted light 686 to indicate the status of the eye-mountable device.

In some examples, the photodetector 672 and the light source 676 can be used as a communication means between the eye-mountable device 610 and one or more external computing devices within a line of sight of the eye-mountable device 610 when the eye-mountable device 610 is contact-mounted on an eye. For example, incident light can pertain to a message to the eye-mountable device 610 and emitted light 686 can pertain to a message from the eye-mountable device 610.

Figure 7A:
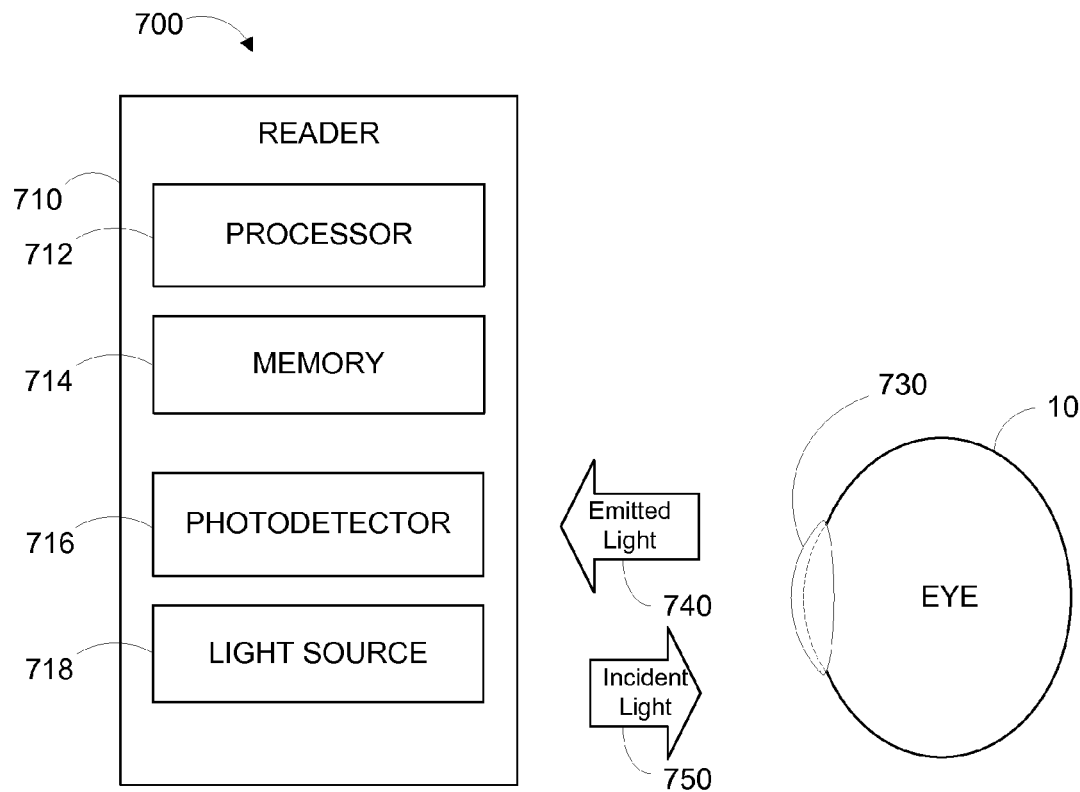
FIG. 7A is a block diagram of an example system 700 with an eye-mountable device and an external reader that are communicating via emitted light by the eye-mountable device and incident light from the external reader.

FIG. 7A is a block diagram of an example system 700 with an eye-mountable device 730 ("body-mountable device") and an external reader 710 that are communicating via emitted light 740 by the eye-mountable device 730 and incident light 750 from the external reader 710. The eye-mountable device 730 can be configured to be contact-mounted over a corneal surface of an eye 10. The eye-mountable device 730 can be configured to receive instructions from the external reader 710 via the incident light 750, and modulate emitted light 740 to communicate, for example, information to the external reader 710.

The external reader 710 includes a processor 712 and a memory 714. The processor 712 can be a computing system that executes software stored in the memory 714 to cause system 700 to communicate, as described herein, information from the external reader 710 to the eye-mountable device 730 via the incident light 750 emitted by a reader light source 718. For example, the incident light 750 may correspond to instructions from the external reader 710 to the eye-mountable device 730. The external reader 710 can be configured to provide the incident light 750 by modifying an aspect of the incident light 750 (e.g., color, brightness, intensity, duration, etc.) emitted by the reader light source 718. The reader photodetector 716 can be configured to receive the emitted light 740. The reader light source 718 can be configured to provide the incident light 750.

Figure 7B:
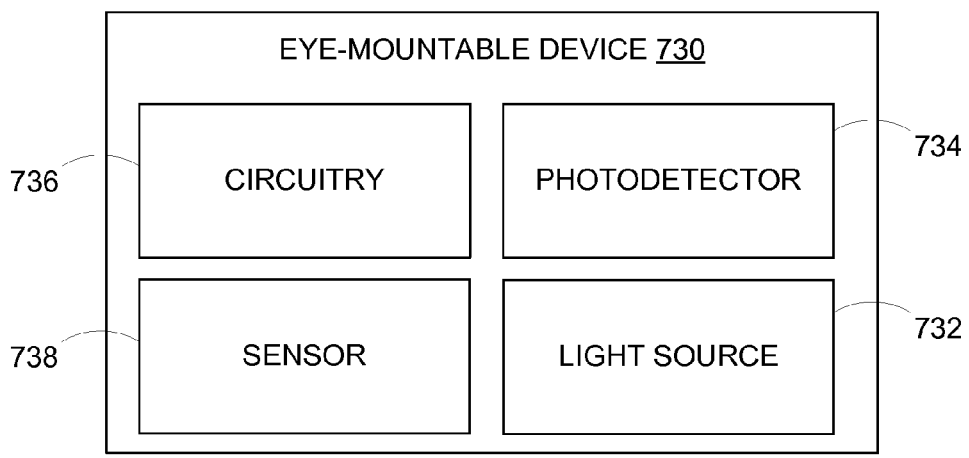
FIG. 7B is a block diagram of the eye-mountable device 730 described in connection with FIG. 7A.

FIG. 7B is a block diagram of the eye-mountable device 730 described in connection with FIG. 7A. The eye-mountable device 730 includes an outward facing light source 732, a photodetector 734, circuitry 736, and a sensor 738. The outward-facing light source 732 provides the emitted light 740 as described in FIG. 7A. The photodetector 734 can be configured to receive the incident light 750 (shown in FIG. 7A) that pertains to the communication from the external reader 710 in FIG. 7A. Circuitry 736 can be configured to determine modulation instructions for the light source 732 based on the received incident light 750. Circuitry 736 can also be configured to modulate the emitted light 740 by controlling the light source 732 to communicate information to the external reader 710. The light source 732 can be configured to provide the emitted light 740 by modifying an aspect of the emitted light 740 (e.g., color, brightness, intensity, duration, etc.). Sensor 738 can be a sensor embedded in the eye-mountable device 730 and configured to provide a reading to the circuitry 736. For example, the circuitry 736 can be configured to obtain the reading from the sensor 738 and communicate the reading to the reader 710 in FIG. 7A by modulating the emitted light 740 from the light source 732.

System 700 can be configured to communicate information between the external reader 710 and the eye-mountable device 730, respectively, via the incident light 750 and the emitted light 740. For example, where the external reader 710 is a computing device in a field of view of the eye-mountable device 730 (e.g., head-mounted device, wearable device, hand-held device, desktop computer, etc.), some example communication scenarios are described below.

In a first example, the external reader 710 can be configured to interrogate the eye-mountable device 730 by modulating the incident light 750 from the reader light source 718. The circuitry 736 included in the eye-mountable device 730 can be configured to receive instructions from the external reader 710 based on the incident light 750 received via the photodetector 734. For example, the circuitry 736 can be configured to obtain a reading from the sensor 738 based on the received instructions. The sensor 738 can be configured to provide to the circuitry 736 the reading indicating biological vitals (e.g., blood pressure, heart rate, temperature, glucose level, psychological state, etc.) of a user of the eye-mountable device 730. The circuitry 736 can be configured to modulate the emitted light 740 from the light source 732 to indicate the reading of the sensor 738. The external reader 710 can receive the emitted light 740 via the reader photodetector 716 and display the biological vitals to the user via a display included in the reader (not shown in FIG. 7A).

In a second example similar to the first example, the reading of the sensor 738 may relate to an ambient environment of the user. For example, the reading may indicate humidity, temperature, ambient light intensity, etc. The external reader 710 can be configured to display information relating to the ambient environment to the user.

In a third example, the emitted light 740 from the eye-mountable device 730 can be used by the external reader 710 to determine a line of sight (LOS) of the user of the eye-mountable device. For example, where the external reader 710 includes a display (e.g., head mounted display) not shown in FIG. 7A, the external reader 710 can determine the line of sight of the user looking at the display. Thus, in this example, the external reader 710 can determine what portion of the display the user is looking at.

In a fourth example, the emitted light 740 from the eye-mountable device 730 can be indicative of a status of the eye-mountable device 730. For example, the emitted light 740 can indicate if one or more components of the eye-mountable device 730 are malfunctioning (e.g., consuming more power than expected).

Figure 8:
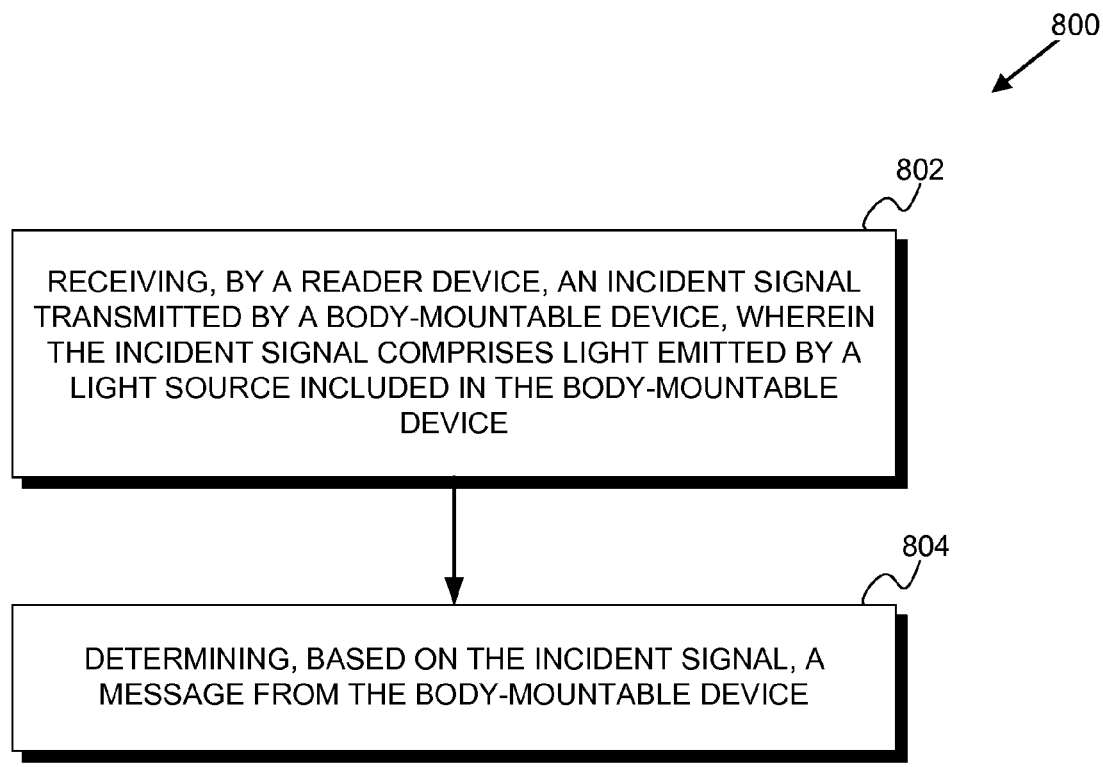
FIG. 8 is a block diagram of an example method 800 for operating an external reader to receive an incident signal transmitted by a body-mountable device, in accordance with at least some embodiments described herein.

FIG. 8 is a block diagram of an example method 800 for operating an external reader to receive an incident signal transmitted by a body-mountable device, in accordance with at least some embodiments described herein. Method 800 shown in FIG. 8 presents an embodiment of a method that could be used with the devices 190, 510, and 710, for example. Method 800 may include one or more operations, functions, or actions as illustrated by one or more of blocks 802-804. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 800 and other processes and methods disclosed herein, the flowchart shows functionality and operation of one possible implementation of present embodiments. In this regard, each block may represent a module, a segment, or a portion of a manufacturing or operation process.

At block 802, the method 800 includes receiving, by a reader device, an incident signal transmitted by a body-mountable device, wherein the incident signal comprises light emitted by a light source included in the body-mountable device.

At block 804, the method 800 includes determining, based on the incident signal, a message from the body-mountable device.

For example, the body-mountable device may send modulated light ("incident signal") towards the external reader indicative of a status of the body-mountable device (step 802). For example, the body-mountable device may be low on power and the modulated light may indicate to the external reader that the body-mountable device is low on power. The reader device may determine the message (e.g., low power) based on the modulated light ("incident signal") (step 804). Although not illustrated in FIG. 8, in some examples, the body-mountable device may include a photodetector to receive incident light ("incident signal"). The method 800 may determine the message based on the incident light on the photodetector.

Figure 9:
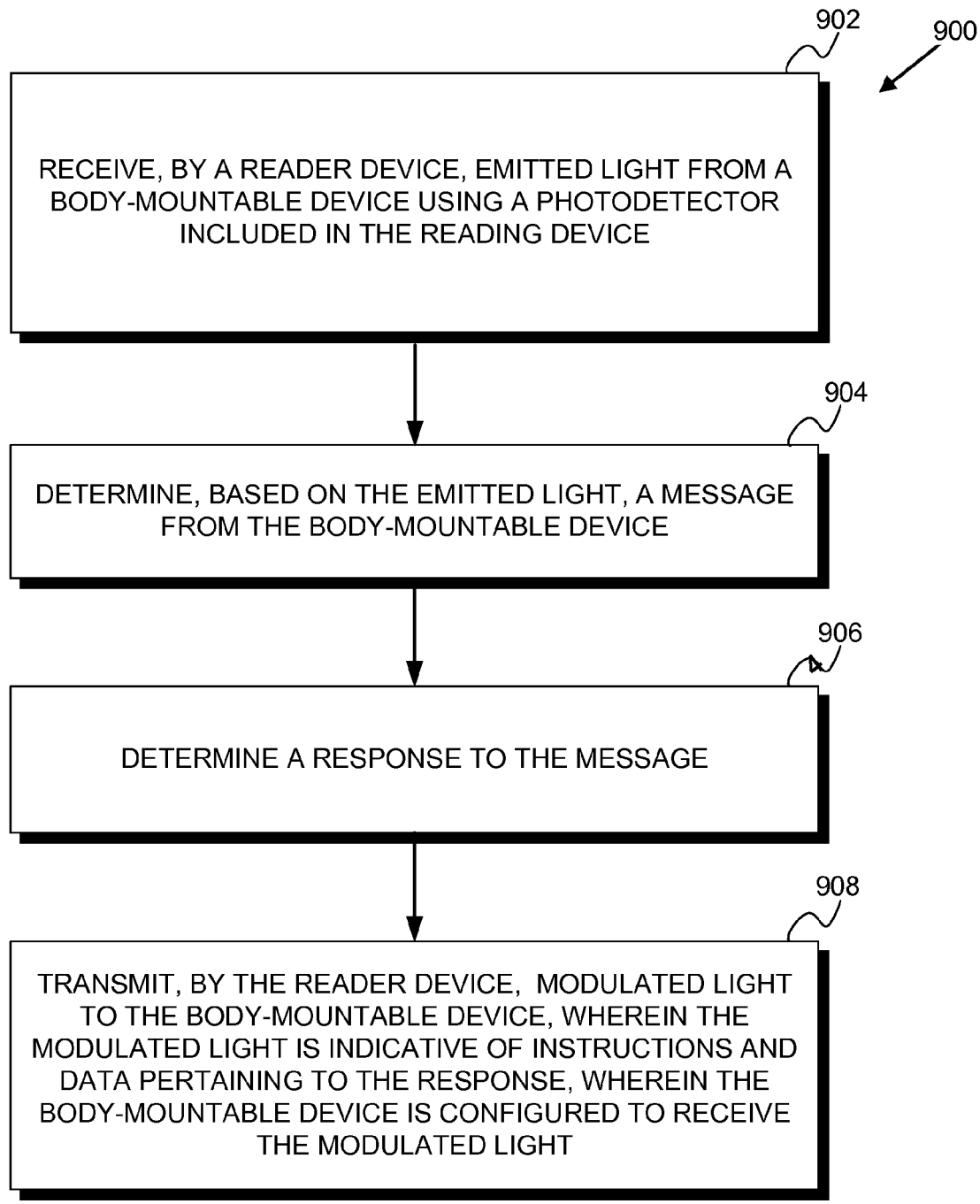
FIG. 9 is a block diagram of an example method 900 for operating an external reader to communicate, via light, with a body-mountable device, in accordance with at least some embodiments described herein.

FIG. 9 is a block diagram of an example method 900 for operating an external reader to communicate, via light, with a body-mountable device, in accordance with at least some embodiments described herein. Method 900 shown in FIG. 9 presents an embodiment of a method that could be used with the devices 190, 510, and 710, for example. Method 900 may include one or more operations, functions, or actions as illustrated by one or more of blocks 902-908. Although the blocks are illustrated in a sequential order, these blocks may in some instances be performed in parallel, and/or in a different order than those described herein. Also, the various blocks may be combined into fewer blocks, divided into additional blocks, and/or removed based upon the desired implementation.

In addition, for the method 900 and other processes and methods disclosed herein, the flowchart shows functionality and operation of one possible implementation of present embodiments. In this regard, each block may represent a module, a segment, or a portion of a manufacturing or operation process.

At block 902, a reader device receives emitted light from a body-mountable device using a photodetector included in the reading device.

At block 904, the reader device determines, based on the emitted light, a message from the body-mountable device.

At block 906, the reader device determines a response to the message.

At block 908, the reader device transmits modulated light to the body-mountable device, wherein the modulated light is indicative of instructions and data pertaining to the response, wherein the body-mountable device is configured to receive the modulated light.

For example, the reader device can be a portable computing device (e.g., laptop, hand held device, etc.) configured to receive emitted light from the body-mountable device using the photodetector included in the portable computing device (step 902). The reader device can determine from the emitted light that a status of the body-mountable device is idle (step 904). The reader device may then determine a response to the message (step 906) indicative of instructions to modify the emitted light by the body-mountable device to a green color to indicate the status of the device. The reader device may transmit the response (step 908) by providing modulated light to the body-mountable device that is configured to receive the modulated light such that the body-mountable device emits the green color.

Figure 10:
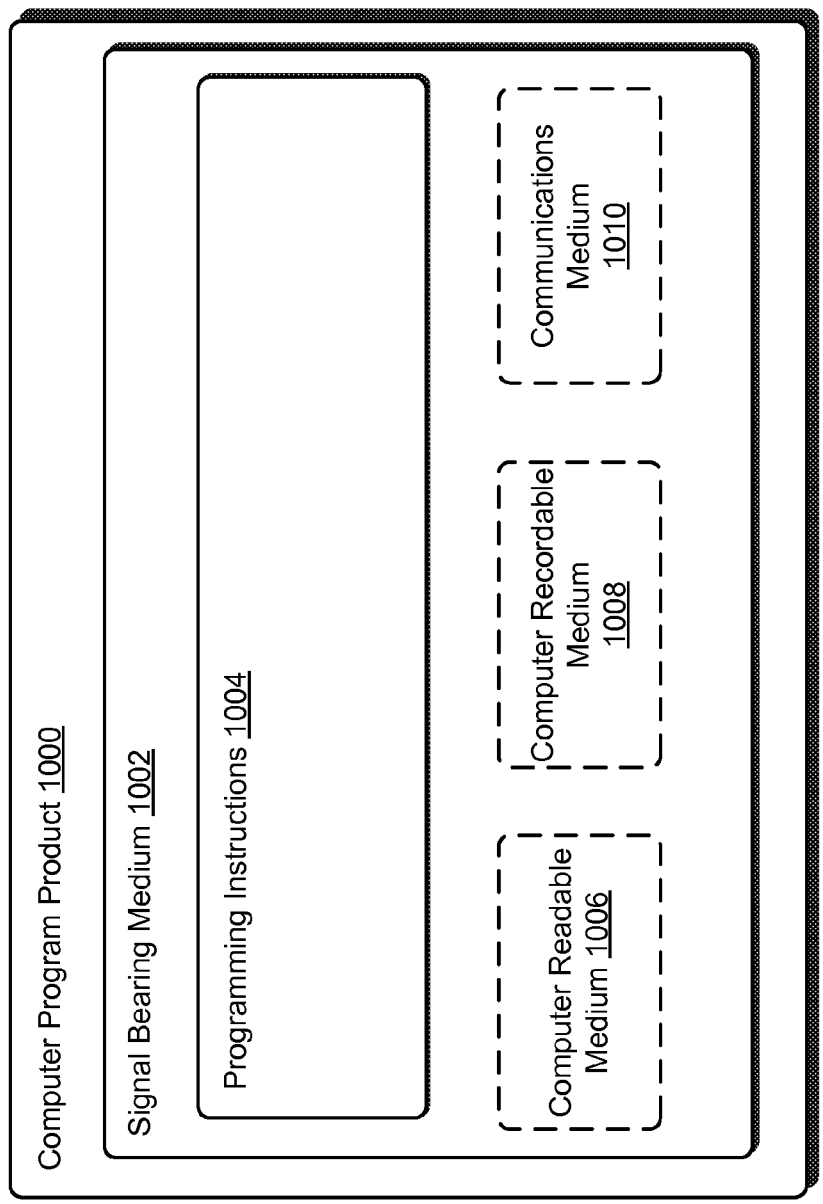
FIG. 10 depicts an example computer-readable medium configured according to at least some embodiments described herein.

FIG. 10 depicts an example computer-readable medium configured according to at least some embodiments described herein. In example embodiments, the example system can include one or more processors, one or more forms of memory, one or more input devices/interfaces, one or more output devices/interfaces, and machine readable instructions that when executed by the one or more processors cause the system to carry out the various functions tasks, capabilities, etc., described above.

As noted above, in some embodiments, the disclosed techniques (e.g. methods 300, 400, 800, and 900) can be implemented by computer program instructions encoded on a non-transitory computer readable storage media in a machine-readable format, or on other non-transitory media or articles of manufacture (e.g., the instructions stored on the memory storage 514 of the reader 510 of the system 500). FIG. 10 is a schematic illustrating a conceptual partial view of an example computer program product that includes a computer program for executing a computer process on a computing device, arranged according to at least some embodiments disclosed herein.

In one embodiment, the example computer program product 1000 is provided using a signal bearing medium 1002. The signal bearing medium 1002 may include one or more programming instructions 1004 that, when executed by one or more processors may provide functionality or portions of the functionality described above with respect to FIGS. 1-9. In some examples, the signal bearing medium 1002 can be a non-transitory computer-readable medium 1006, such as, but not limited to, a hard disk drive, a Compact Disc (CD), a Digital Video Disk (DVD), a digital tape, memory, etc. In some implementations, the signal bearing medium 1002 can be a computer recordable medium 1008, such as, but not limited to, memory, read/write (R/W) CDs, R/W DVDs, etc. In some implementations, the signal bearing medium 1002 can be a communication medium 1010 (e.g., a fiber optic cable, a waveguide, a wired communications link, a wireless communication link, etc.). Thus, for example, the signal bearing medium 1002 can be conveyed by a wireless form of the communications medium 1010.

The one or more programming instructions 1004 can be, for example, computer executable and/or logic implemented instructions. In some examples, a computing device such as the processor-equipped external reader 190 of FIG. 1 is configured to provide various operations, functions, or actions in response to the programming instructions 1004 conveyed to the computing device by one or more of the computer readable medium 1006, the computer recordable medium 1008, and/or the communications medium 1010.

The non-transitory computer readable medium 1006 can also be distributed among multiple data storage elements, which could be remotely located from each other. The computing device that executes some or all of the stored instructions could be an external reader such as the reader 190 illustrated in FIG. 1, or another mobile computing platform, such as a smartphone, tablet device, personal computer, head-mounted device, etc. Alternatively, the computing device that executes some or all of the stored instructions could be remotely located computer system, such as a server. For example, the computer program product 1000 can implement the functionalities discussed in the description of FIGS. 1-9.

Within examples, operation methods that are described for the device can be applied to other electronic devices that include an outward-facing light source. For example, implantable devices that measure biological information can include a light source directed outwards from a body where the implantable devices are implanted. Thus, example methods herein provide operation methods that involve an outward-facing light source, receiving modulation instructions, and modulating light emitted by the outward-facing light source based on the modulation instructions.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location) and an opportunity to control whether or how personal information is used. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and how the collected information is used.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
receiving, by a photodetector in a reader device, an incident signal transmitted by a body-mountable device, wherein the body-mountable device includes a transparent material, a substrate at least partially embedded in the transparent material, and a light source disposed on the substrate, wherein the transparent material has a mounting surface and a surface opposite the mounting surface, and wherein the incident signal comprises light emitted by the light source and transmitted through the surface opposite the mounting surface; and
determining, by the reader device, a message from the body-mountable device based on the incident signal received by the photodetector.

2. The method of claim 1, wherein the light emitted by the light source and transmitted through the surface opposite the mounting surface is modulated with respect to at least one of a color, brightness, intensity, or duration.

3. The method of claim 2, wherein the body-mountable device includes circuitry disposed on the substrate, wherein the circuitry is configured to modulate the light emitted by the light source.

4. The method of claim 3, further comprising:
transmitting, by the reader device, data to the body-mountable device; and
transmitting, by the reader device, instructions to the body-mountable device, wherein the instructions are configured to cause the circuitry to modulate the light emitted by the light source based on the data.

5. The method of claim 4, further comprising determining a response to the message, wherein the data and the instructions are indicative of the response.

* * * * *